United States Patent [19]

Niwa

[11] Patent Number: 5,379,113

[45] Date of Patent: Jan. 3, 1995

[54] PARTICLE SIZE MEASURING DEVICE

[75] Inventor: Takeshi Niwa, Kyoto, Japan

[73] Assignee: Shimadzu Corporation, Kyoto, Japan

[21] Appl. No.: 123,097

[22] Filed: Sep. 20, 1993

[30] Foreign Application Priority Data

Sep. 28, 1992 [JP] Japan .................................. 4-257877

[51] Int. Cl.$^6$ ............................................. G01N 15/02
[52] U.S. Cl. .................................. 356/336; 356/343;
250/574
[58] Field of Search ............... 356/335, 336, 337, 338,
356/339, 340, 341, 342, 343; 364/555; 250/574,
222.2; 377/11; 73/865.5, 866, 865.8

[56] References Cited

U.S. PATENT DOCUMENTS

| | | | |
|---|---|---|---|
| 4,188,121 | 2/1980 | Hirleman, Jr. et al. | 356/336 |
| 4,288,162 | 9/1981 | Sakamoto et al. | 356/335 |
| 4,595,291 | 6/1986 | Tatsuno | 356/336 |
| 5,105,093 | 4/1992 | Niwa | 356/336 |
| 5,164,787 | 11/1992 | Igushi et al. | 356/336 |

FOREIGN PATENT DOCUMENTS

| | | | |
|---|---|---|---|
| 0174937 | 7/1989 | Japan | 356/336 |
| 4084735 | 3/1992 | Japan | 356/336 |

Primary Examiner—Richard A. Rosenberger
Assistant Examiner—Hoa Q. Pham
Attorney, Agent, or Firm—Nikaido, Marmelstein, Murray & Oram

[57] ABSTRACT

A particle size measuring device which includes a laser and photo-sensors for measuring the spatial intensity distribution of diffracting and scattering light upon the specimen. An arithmetic unit is provided for calculating particle size distribution on the basis of the measured spatial intensity distribution, and a first judging device for monitoring outputs from selected photo-sensors so as to see if the monitored outputs exceed a first reference so as to know that the specimen is present in the optical system. A second judging device is use for storing the outputs of all the photo-sensors when the specimen is present in the optical system, and seeing if a maximum value of the outputs falls within a range defined by a second and third reference so as to know that the concentration of the specimen is optimal for measuring. A storage device is provided for storing the outputs of all the photo-sensors as effective data only when the maximum value falls within the reference range, and a third judging device is provided for seeing if predetermined sets of effective data have been stored in the storage. The arithmetic unit is operated when it is found that the predetermined sets of effective data are stored in the storage.

3 Claims, 5 Drawing Sheets

PARTICLE SIZE MEASURING DEVICE

FIELD OF THE INVENTION

The present invention relates generally to a device for measuring particle size distribution of powdery solids by utilizing diffracting and scattering light that occurs owing to the presence of the powdery solids. The measuring device is particularly adapted for measuring particle size distribution of powdery solids in a dry state.

BACKGROUND OF THE INVENTION

It is known in the art that the particle size distribution of powdery solids is measured by utilizing light diffraction singly or diffraction and light scattering jointly each of which tends to occur when powdery solids afloat in dispersion is irradiated with laser beam. More specifically, the laser beam diffracts and scatters owing to the presence of powdery solids, and the spatial intensity distribution of the diffracting and scattering light is detected by photo-sensors such as ring detectors. The resulting data are converted into particle size distribution in terms of functions based on the Fraunhofer's diffraction theory or the Mie light scattering theory.

The known measuring devices necessarily uses a liquid dispersion agent so as to disperse the powdery solids, hereinafter referred to as "specimen", and the method using a liquid dispersing agent will be referred to as "wet measuring method". If the specimen is a type which tends to become dissolved or hardened at the presence of liquid, which is common with medicinal substances and cement, a liquid dispersing agent is substituted by air, hereinafter referred to as "dry measuring method".

In order to carry out the dry measuring method, a group of particles are obtained as a specimen from the powdery solids by dispersing them into a misty state (hereinafter called "aerosol particles") and the aerosol particles are irradiated with laser beam.

This known measuring method requires that the specimen has a constant concentration in a predetermined range.

The wet measuring method makes it easy to homogeneously disperse the specimen, and to maintain the concentration of it within a required range. The dry measuring method is difficult to keep the concentration of specimen in a particular range unless a special sampling device is employed. Even though a special sampling device is employed, the concentration of specimen is difficult to maintain because of unexpected factors such as unstable pneumatic pressure, improper handling of the sampling device and malfunction thereof. There are a kind of powders whose concentration is inherently unstable after they are ejected in aerosol, which results in imprecise measurement.

SUMMARY OF THE INVENTION

The present invention is directed to overcome the difficulty in measuring the particle size distribution of powdery solids in a dry state regardless of any change in the concentration thereof.

According to the present invention, the measuring device includes a laser for radiating laser beam upon a specimen, an optical measuring system comprising a plurality of photo-sensors for measuring the intensity distribution of diffracting and scattering light upon the specimen, an arithmetic unit for calculating particle size distribution of the specimen on the basis of the intensity distribution measured by the optical measuring system, a first judging means for monitoring outputs from a predetermined number of photo-sensors and seeing if the monitored outputs exceed a first reference so as to know that the specimen is present in the optical measuring system, a second judging means for storing the outputs of all the photo-sensors after the first judging means ascertains that the specimen is present in the optical measuring system, and seeing if a maximum value of the outputs falls between a second reference and a third reference so as to know that the concentration of the specimen is optimal for measuring, a storage for storing the outputs of all the photo-sensors as effective data when the second judging means ascertains that the maximum value is present between the second and third reference, a third judging means for seeing if predetermined sets of effective data have been stored in the storage, and wherein the arithmetic unit is performed when predetermined sets of effective data have been stored in the storage.

BRIEF DESCRIPTION OF THE DRAWINGS

This invention may be better understood and its numerous objects and advantages will become apparent to those skilled in the art by reference to the accompanying drawings as follows.

DETAILED DESCRIPTION OF THE PREFERRED EMBODIMENT

Figure 1:
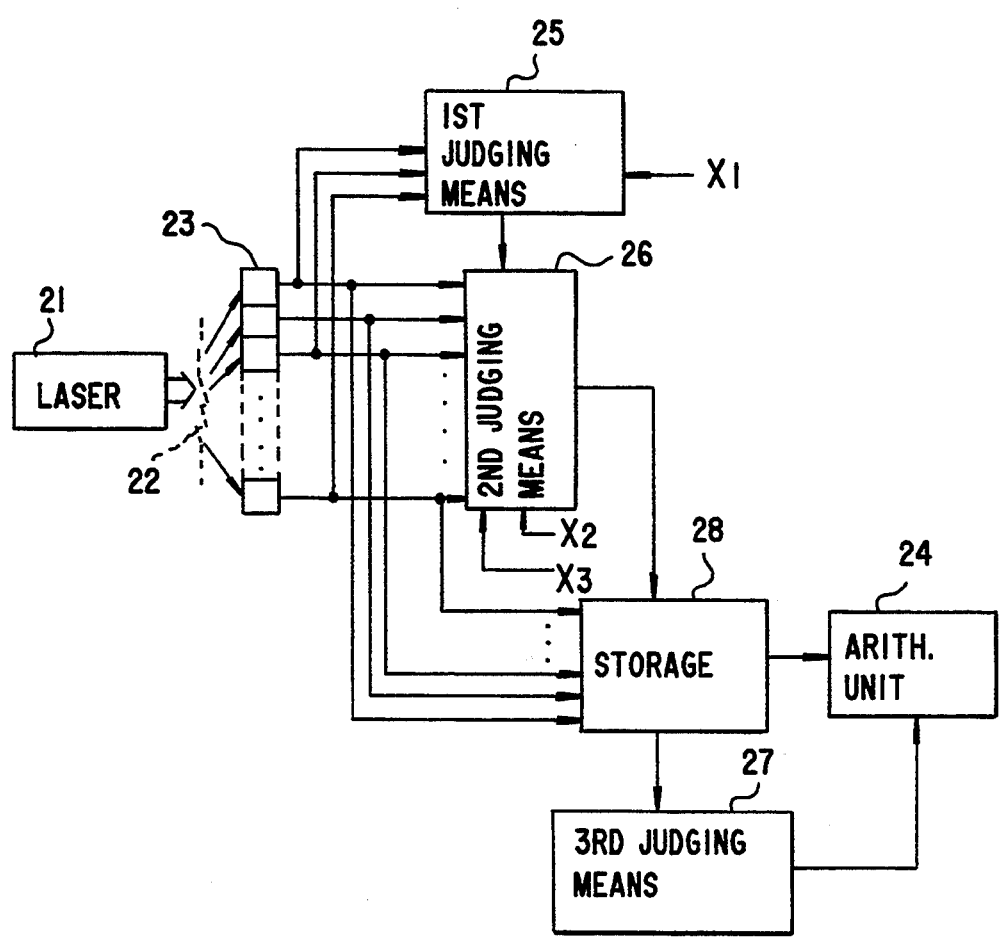
FIG. 1 is an explanatory view exemplifying the principle underlying the present invention.

Referring to FIG. 1, the basic principle underlying the present invention will be described:

There is provided a laser 21 which generates laser beam against a group of powder solids (specimen) 22. The laser beam diffracts and scatters owing to the presence of the specimen 22, and the spatial intensity distribution of diffracting and scattering light is measured by photo-sensors 23. The spatial intensity distribution is arithmetically processed so as to convert into the particle size distribution of the specimen. There are three judging means 25, 26 and 27 and a storage 28. The data of the spatial intensity distribution of diffracting and scattering light are selected in accordance with the results of each judging means 25, 26 and 27, and the effective data alone are stored in the storage 28. After the storage 28 stores predetermined sets of effective data, they are converted into the particle size distribution of the specimen by an arithmetic unit 24.

More specifically, the first judging means 25 monitors outputs of a predetermined number of photo-sensors 23 so as to see if they exceed a first reference value $X_1$ and ascertain that the specimen is present in the optical measuring system. The second judging means 26 monitors the outputs of all the photo-sensors 23, and sees if the maximum value falls within a range defined by a second reference value $X_2$ and a third reference value $X_3$, thereby ascertaining that the concentration of the specimen falls within the required range. The storage 28 stores the outputs of all the photo-sensors 23 as effective data only when the second judging means 26 ascertains that the maximum value falls within the required range, that is, between the second reference value $X_2$ and the third reference value $X_3$. The third judging means 27 sees if predetermined sets of effective data have been stored.

Figure 5:
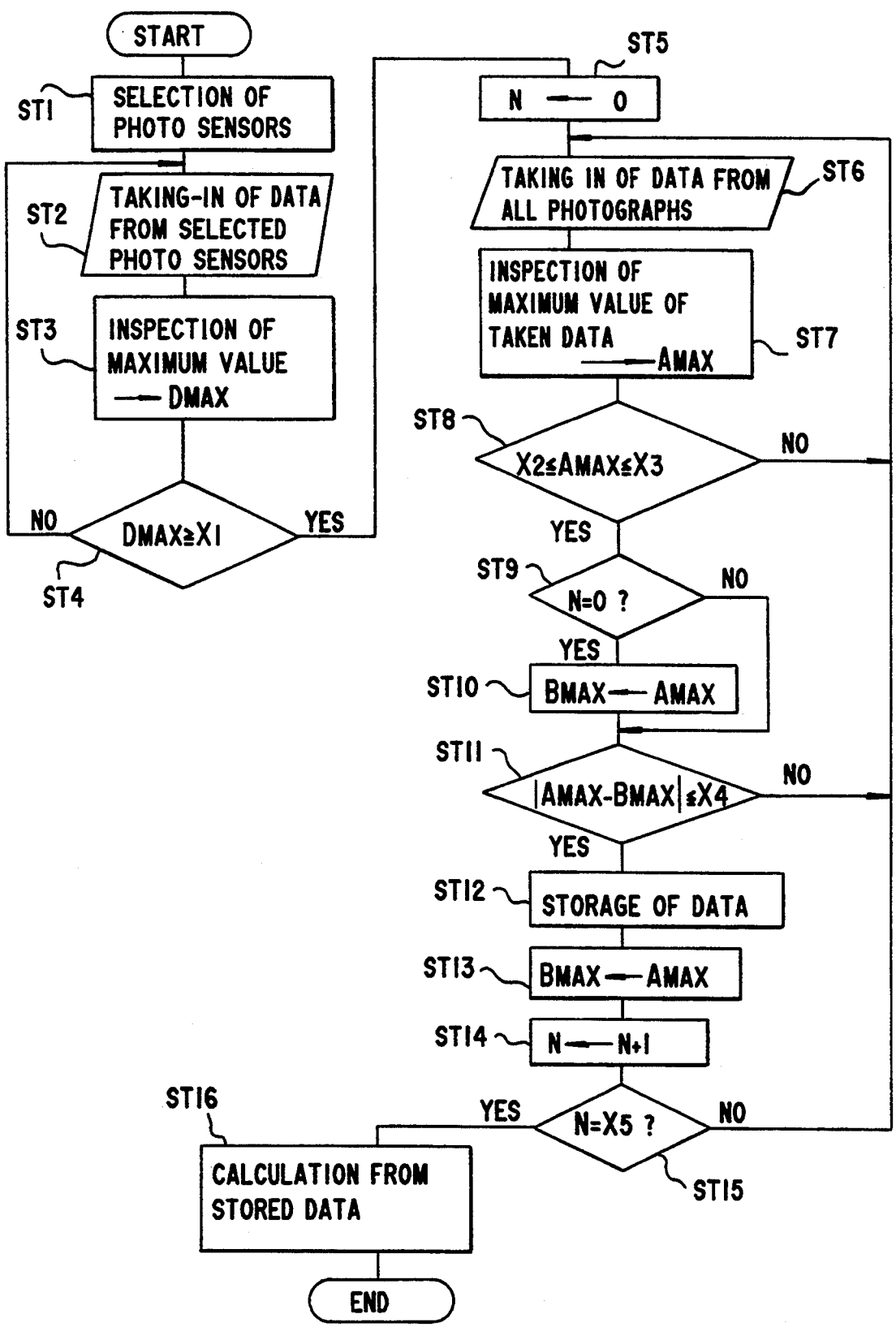
FIG. 5 is a flowchart showing a program written in a computer incorporated in the present invention.

The relations between the maximum value of all the outputs of the photo-sensors 23 and the existing concentration of the specimen are depicted in straight line as shown in FIG. 5.

Thus, even if the concentration of aerosol particles varies, the storage 28 stores the spatial intensity distributions of diffracting and scattering light that are obtained so long as the concentration of the specimen falls within the required range. When desired sets of effective data are stored, the stored data are converted into the particle size distribution of the specimen.

Figure 2:
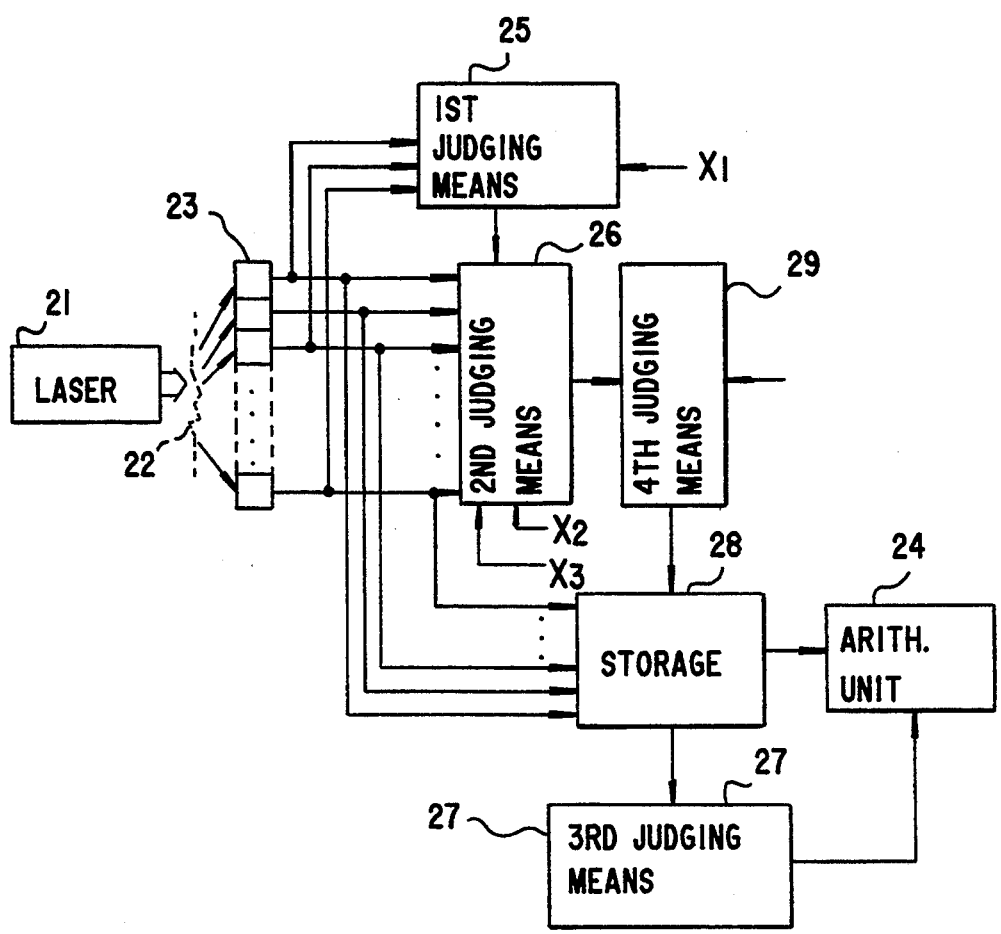
FIG. 2 is an explanatory view showing another example of the embodiment.

An alternative embodiment shown in FIG. 2 is additionally provided with a fourth judging means 29 located subsequent to the second judging means 26. The fourth judging means 29 compares the maximum output $A_{max}$ of those of all the photo-sensors 23 with the maximum output $B_{max}$ of them in the corresponding previous situation where the second judging means 26 ascertains that the concentration of the specimen falls within the required range. The fourth judging means 29 sees if the difference ($A_{max} - B_{max}$) between the values $A_{max}$ and $B_{max}$ remains within a fourth value $X_4$. When the difference remains within the fourth value $X_4$, the outputs of all the photo-sensors 23 are stored in the storage 28 as effective data on the spatial intensity distribution of diffracting and scattering light.

The addition of the fourth judging means 29 is advantageous in widening the reference range $X_2-X_3$ so as to enable the second judging means 26 to judge the concentration of specimen in a wider range.

Figure 3:
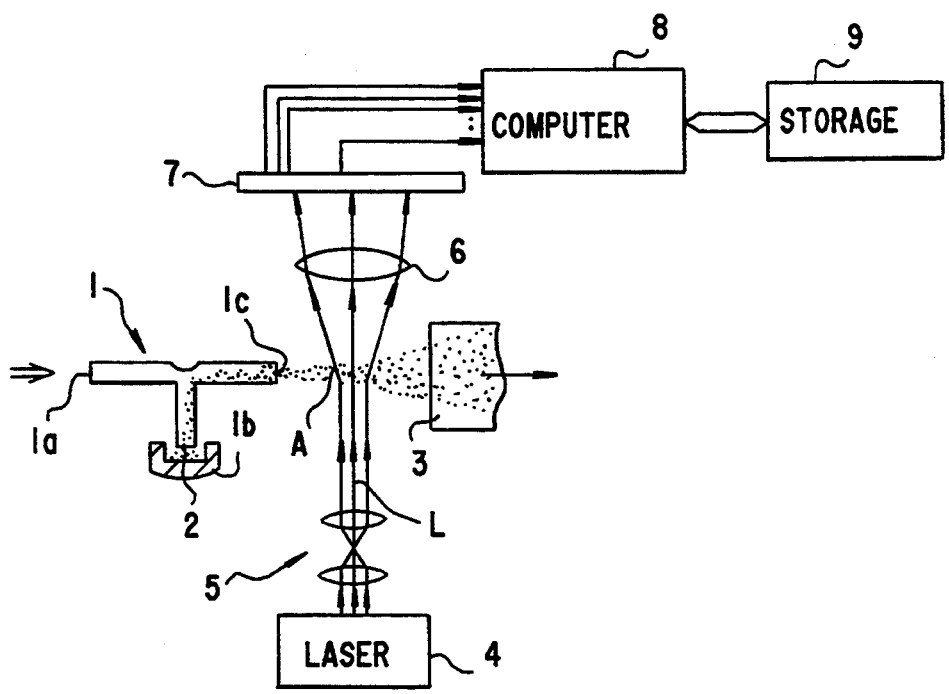
FIG. 3 is a diagrammatical view showing the structure of an embodiment according to the present invention.

Referring to FIG. 3, the structure of the measuring device according to the present invention will be described, wherein different numerals from those in FIGS. 1 and 2 are used to designate the same components:

An ejector 1 includes an air inlet 1a connected to an air compressor (not shown), a powdery solids supply port 1b located adjacent to a powder supplier 2, and a powdery solids outlet 1c through which powdery solids (A) are ejected in aerosol under pneumatic compression through the air inlet 1a. The aerosol particles (A) are ejected by the ejector 1 toward a collector 3, and are collected therein.

An optical measuring system is placed in such a manner that the optical axis (L) is located between the outlet 1c and the collector 3. A laser 4 generates a flux of laser beam against the aerosol particles through a beam flux forming optical system 5 (hereinafter referred to as "optical system") wherein the flux of laser beam has a predetermined cross-sectional area in parallel with the optical axis (L). A condenser lens 6 and a ring detector 7 are located on the optical axis (L) on the opposite side of the optical system 5 with the aerosol particles (A) interposed therebetween, wherein the ring detector 7 is located on the focal surface of the condenser lens 6. The ring detector 7 allows an image to be formed by light diffracting and/or scattering which occurs owing to the aerosol particles.

Figure 4:
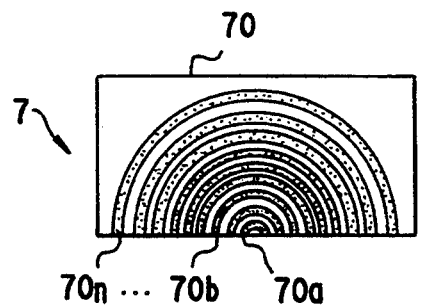
FIG. 4 is a front view showing ring detectors used in the present invention.

Referring to FIG. 4, the ring detector 7 has a plurality of photo-sensors $70a \ldots 70n$ having semi-circular or circular light receptive surfaces on a base plate 70. The spatial intensity distribution of the aerosol particles caused by diffraction singly or diffraction and light scattering jointly is measured by obtaining the amplitude of the outputs of the photo-sensors $70a \ldots 70n$.

The outputs of the photo-sensors $70a \ldots 70n$ in the ring detector 7 are digitized through an A/D converter (not shown) which are taken into a computer 8 at predetermined time intervals where necessary data alone are extracted from the data obtained in this way and stored in a storage 9 in accordance with a program which will be described hereinafter. The data stored in the storage 9 is used to calculate the particle size distribution.

Referring to FIG. 5, the measuring device is driven prior to starting the ejection of aerosol (A) through the ejector 1 and a predetermined number of photo-sensors $70a \ldots 70n$ are selected from those in the ring detector 7. The output data of the selected photo-sensors are temporarily stored in at ST1 and ST2 among which the maximum value $D_{max}$ is searched at ST3.

The obtained maximum value $D_{max}$ is compared with a predetermined value $X_1$ at ST4. This value $X_1$ is intended to detect the presence of particles between the optical system 5 and the condenser lens 6 through an increase in the spatial intensity of light incident to each photo-sensor due to the diffraction singly or the diffraction and scattering jointly. When the maximum value $D_{max}$ does not reach the value $X_1$, the same sequence from ST2 is repeated. When the maximum value $_{max}$ reaches the value $X_1$, the sequence advances to a concentration checking routine at step ST5 and below.

In the concentration checking routine the number of times of measurements (N) is reset to 0 (zero)(ST5), and the data from the photo-sensors in the ring detectors 7 are temporarily stored to search the maximum value $A_{max}$ at ST6 and ST7. At ST8 it is checked to see if the maximum value $A_{max}$ is present between predetermined values $X_2$ and $X_3$.

Figure 6:
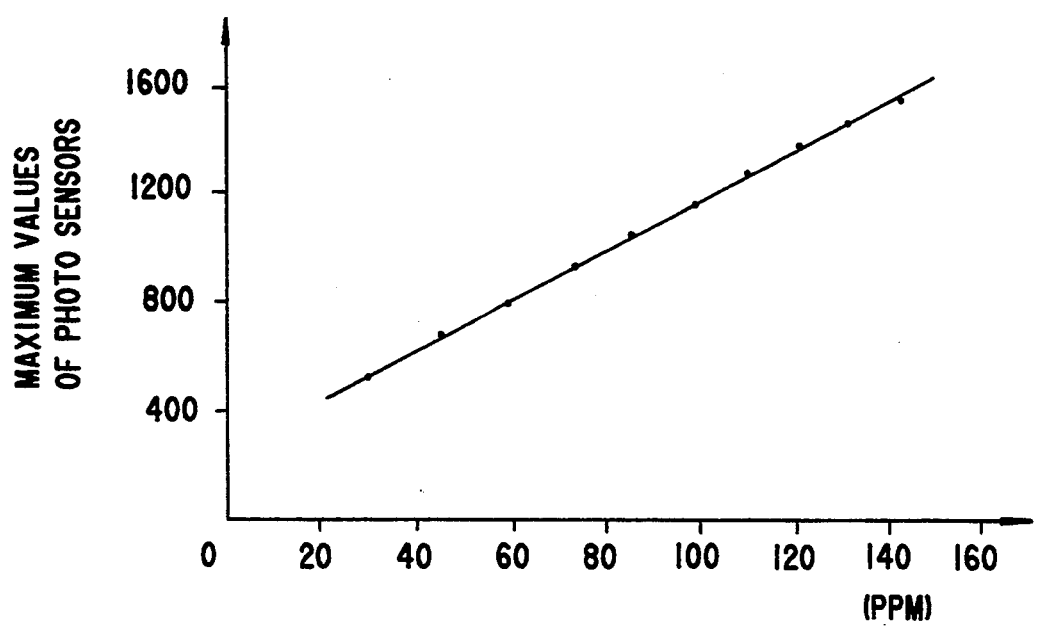
FIG. 6 is a graph showing a relationship between concentration and maximum values of outputs from photo-sensors in a dry measuring method under the present invention.

The values $X_2$ and $X_3$ correspond to the lower limit and the upper limit of an optimal range which determines an optimal range of the concentration of powdery solids. The relations between the maximum values $A_{max}$ of outputs from the photo-sensors and the concentrations of powdery solids are shown in graph in FIG. 6. It will be understood from the graph that the relations are proportional as seen from the straight line within the predetermined range of concentration. On the basis of this linear relationship the values $X_2$ and $X_3$ are set so as to correspond to the optimal measuring range.

At ST8, if it is found that the value $A_{max}$ does not fall within the range defined by the values $X_2$ and $X_3$, the sequence is returned to ST6 where the check is repeated. If it is found that the maximum value $A_{max}$ exists between the values $X_2$ and $X_3$, the sequence advances to ST9 on the understanding that the optimal measuring range is reached.

At ST9 and below where various concentration ranges are checked, when N (number of times of measurement) is 0 (zero), which means that the concentration of powdery solids falls within the optimal range for the first time after the measurement is initiated, the maximum value $A_{max}$ is compared with a previous maximum value $B_{max}$ if it exists, and if it does not exist, the maximum value $A_{max}$ is compared with itself, a difference between the two maximum values is obtained, and compared with a value $X_4$ at ST11, wherein the value $X_4$ determines a range covering a sudden or unexpected change likely to occur in the optimal measuring range, thereby negating data arising from such sudden change. If the difference ($A_{max}-B_{max}$) is equal to or smaller than the value $X_4$, the data from all the photo-sensors temporarily stored at ST6 are stored in the storage 9 at ST12, and the maximum value $A_{max}$ is stored at ST13 as the maximum value $B_{max}$ for subsequent comparison. One is added to N (number of times) at ST14, and the same sequence below ST6 is repeated. When N is 0, meaning that $A_{max}$ is equal to $B_{max}$, the data is stored.

When N is 1 and more, and if the concentration of powdery solids exceeds the allowable range with the result that the difference between $A_{max}$ and $B_{max}$ exceeds the value $X_4$. The data are not stored, and the sequence from ST6 is repeated.

In this way the data is continuously stored in the storage 9 so long as the concentration of powdery solids is within the optimal range, and variation thereof, if any, remain within the allowable range after the previous data are stored. When the number of times (N) reaches $X_5$ times (normally a few hundreds of times), the data in the storage 9 are used, and particle size distribution is calculated by a known arithmetic method (ST15 and ST16).

The present invention measures particle size distribution with precision regardless of any variation occurring in the concentration of powdery solids ejected in aerosol through the ejector 1.

Instead of the concentration checking routine and the concentration allowable range checking routine, the latter can be omitted if the values $X_2$ and $X_3$ in the concentration checking routine are narrowly set so as to provide a narrow optimal range. If the maximum value $A_{max}$ falls within this narrow range, it means that the value $A_{max}$ is virtually the same as the value $B_{max}$. Thus the same effect is obtained as that resulting from the example described above.

What is claimed is:

1. A device for measuring particle size distribution of powdery solids, the device comprising:

a laser for radiating laser beam upon a specimen of the powdery solids;

an optical measuring system including a plurality of photo-sensors for measuring a spatial intensity distribution of diffracting and scattering light upon the specimen;

an arithmetic unit for calculating a particle size distribution of the specimen on the basis of the spatial intensity distribution measured by the photo-sensors;

a first judging means for monitoring outputs from a predetermined number of photo-sensors and seeing if the monitored outputs exceed a first reference so as to know that the specimen are present in the optical measuring system;

a second judging means for storing the outputs of all the photo-sensors after the first judging means ascertains that the specimen is present in the optical measuring system, and seeing if a maximum value of the outputs falls within a range defined by a second reference and a third reference so as to know that a concentration of the specimen is optimal for measuring;

a storage for storing the outputs of all the photo-sensors as effective data only when the second means ascertains that the maximum value falls within the range defined by the second and third references; and a third judging means for seeing if predetermined sets of effective data have been stored in the storage so as to operate the arithmetic unit.

2. The device according to claim 1, further comprising a fourth judging means for seeing if a difference between the maximum value of all the outputs of the photo-sensors and a previous maximum value is equal to or smaller than a fourth reference, during the period of time when the second judging means ascertains that the concentration of the specimen falls within a required range, wherein the storage stores all the outputs of the photo-sensors as effective data when the difference is equal to or smaller than the fourth reference.

3. The device according to claim 1 or 2, wherein the photo-sensors are constituted by ring detectors having different radii arranged concentric of an optical axis of the optical measuring system.

* * * * *